United States Patent
Frosch et al.

(10) Patent No.: US 9,855,286 B2
(45) Date of Patent: Jan. 2, 2018

(54) PHARMACEUTICAL COMPOSITION COMPRISING (1R,4R)-6'-FLUORO-N,N-DI METHYL-4-PHENYL-4',9'-DIHYDRO-3'H-SPIRO[CYCLOHEXANE-1,1'-PYRANO-[3,4,B]INDOL]-4-AMINE AND A SALICYLIC ACID COMPONENT

(71) Applicant: Gruenenthal GmbH, Aachen (DE)

(72) Inventors: Stefanie Frosch, Aachen (DE); Klaus Linz, Rheinbach (DE); Klaus Schiene, Juechen (DE)

(73) Assignee: Gruenenthal GmbH, Aachen (DE)

( * ) Notice: Subject to any disclaimer, the term of this patent is extended or adjusted under 35 U.S.C. 154(b) by 18 days.

(21) Appl. No.: 13/892,813

(22) Filed: May 13, 2013

(65) Prior Publication Data

US 2013/0317076 A1 Nov. 28, 2013

Related U.S. Application Data

(60) Provisional application No. 61/648,805, filed on May 18, 2012.

(30) Foreign Application Priority Data

May 18, 2012 (EP) .................................. 12 003 936

(51) Int. Cl.
*A61K 31/407* (2006.01)
*A61K 31/60* (2006.01)
(Continued)

(52) U.S. Cl.
CPC .......... *A61K 31/616* (2013.01); *A61K 31/407* (2013.01); *A61K 31/60* (2013.01); *A61K 45/06* (2013.01)

(58) Field of Classification Search
CPC ...... A61K 45/06; A61K 31/60; A61K 31/407; A61K 31/616; A61K 2300/00
(Continued)

(56) References Cited

U.S. PATENT DOCUMENTS 4,389,393 A 6/1983 Schor et al.
4,404,208 A 9/1983 Schmidt
(Continued)

FOREIGN PATENT DOCUMENTS

CN 1671419 A 9/2005
CN 1735619 A 2/2006
(Continued)

OTHER PUBLICATIONS

SciFinder (Chemical Abstracts Services (CAS), substance search of publication US 2013/0317076 A1; the publication of the instant application), performed by Examiner, Aug. 11, 2014. (excerpt in action).*
(Continued)

*Primary Examiner* — Ernst V Arnold
*Assistant Examiner* — Miriam A Levin
(74) *Attorney, Agent, or Firm* — Crowell & Moring LLP (57) ABSTRACT

The invention relates to a pharmaceutical composition comprising a first pharmacologically active ingredient selected from (1r,4r)-6'-fluoro-N,N-dimethyl-4-phenyl-4',9'-dihydro-3'H-spiro[cyclohexane-1,1'-pyrano[3,4,b]indol]-4-amine and the physiologically acceptable salts thereof, and a second pharmacologically active ingredient which is a salicylic acid component selected from the group consisting of acetylsalicylic acid, salicylic acid, salicylamide, ethenzamide, salsalate, dipyrocetyl, benorilate, diflunisal, guacetisal, and the physiologically acceptable salts thereof.

10 Claims, 2 Drawing Sheets

(51) Int. Cl.
*A61K 31/616* (2006.01)
*A61K 45/06* (2006.01)

(58) Field of Classification Search
USPC .................. 514/409, 159, 161, 162, 165
See application file for complete search history.

(56) References Cited

U.S. PATENT DOCUMENTS

| | | | |
|---|---|---|---|
| 4,612,008 | A | 9/1986 | Wong et al. |
| 4,765,989 | A | 8/1988 | Wong et al. |
| 4,778,799 | A | 10/1988 | Tibes et al. |
| 4,783,337 | A | 11/1988 | Wong et al. |
| 5,310,936 | A | 5/1994 | Regtop et al. |
| 5,330,761 | A | 7/1994 | Baichwal |
| 5,339,362 | A | 3/1995 | Baichwal et al. |
| 5,399,362 | A | 3/1995 | Baichwal et al. |
| 5,455,046 | A | 10/1995 | Baichwal |
| 5,472,711 | A | 12/1995 | Baichwal |
| 5,914,129 | A * | 6/1999 | Mauskop ............. 424/464 |
| 6,245,802 | B1 | 6/2001 | Iyengar et al. |
| 6,713,089 | B1 | 3/2004 | Bertelsen et al. |
| 7,332,519 | B2 | 2/2008 | Hinze et al. |
| 7,700,579 | B2 | 4/2010 | Capocchi |
| 9,320,729 | B2 | 4/2016 | Frosch et al. |
| 2005/0192333 | A1 | 9/2005 | Hinze et al. |
| 2006/0004034 | A1* | 1/2006 | Hinze et al. ............. 514/278 |
| 2008/0125475 | A1 | 5/2008 | Linz et al. |
| 2010/0069501 | A1 | 3/2010 | Bloms-Funke et al. |
| 2010/0240897 | A1 | 9/2010 | Hinze et al. |
| 2010/0297252 | A1 | 11/2010 | Cooper et al. |
| 2011/0319440 | A1 | 12/2011 | Hinze et al. |
| 2016/0197349 | A1 | 7/2016 | Schmidt |

FOREIGN PATENT DOCUMENTS

| | | |
|---|---|---|
| CN | 101147735 A | 3/2008 |
| CN | 101198606 A | 6/2008 |
| CN | 101327193 A | 12/2008 |
| CN | 101693714 A | 4/2010 |
| DE | 10 2006 056 458 A1 | 5/2008 |
| EP | 0 068 838 A1 | 1/1983 |
| EP | 0 661 050 A1 | 7/1995 |
| EP | 1 219 304 A2 | 7/2002 |
| EP | 1 457 202 A2 | 9/2004 |
| JP | 59-7119 A | 1/1984 |
| JP | 59-21615 A | 2/1984 |
| JP | 61-172819 A | 8/1986 |
| JP | 5-221857 A | 8/1993 |
| JP | 2001-516699 A | 10/2001 |
| JP | 2002-529499 A | 9/2002 |
| JP | 2006-508114 A | 3/2006 |
| JP | 2009-535312 A | 10/2009 |
| JP | 2009-535313 A | 10/2009 |
| JP | 2010-540668 A | 12/2010 |
| JP | 2012-501985 A | 1/2012 |
| JP | 2012-501986 A | 1/2012 |
| JP | 2012-501987 A | 1/2012 |
| WO | WO 93/00895 A1 | 1/1993 |
| WO | WO 94/29309 A1 | 12/1994 |
| WO | WO 99/13799 A1 | 3/1999 |
| WO | WO 03/064425 A1 | 8/2003 |
| WO | WO 03/105906 A1 | 12/2003 |
| WO | WO 2004/043967 A1 | 5/2004 |
| WO | WO 2004/052356 A1 | 6/2004 |
| WO | WO 2005/066183 A1 | 7/2005 |
| WO | WO 2006/134486 A2 | 12/2006 |
| WO | WO 2007/128412 A1 | 11/2007 |
| WO | WO 2007/128413 A1 | 11/2007 |
| WO | WO 2008/040481 A1 | 4/2008 |
| WO | WO 2009/046801 A1 | 4/2009 |
| WO | WO 2010/025931 A2 | 3/2010 |
| WO | WO 2010/025934 A1 | 3/2010 |
| WO | WO 2012/016695 A3 | 2/2012 |
| WO | WO 2012/016697 A2 | 2/2012 |
| WO | WO 2012/016698 A2 | 2/2012 |
| WO | WO 2012/016703 A3 | 2/2012 |

OTHER PUBLICATIONS

Linz et al., Cebranopadol: A Novel Potent Analgesic Nociceptin / Orphanin FQ Peptide and Opioid Receptor Agonist, The Journal of Pharmacology and Experimental Therapeutics (J Pharmacol Exp Ther), 349: 535-548 (Jun. 2014), 14 pages.*
Mandal, Morphine Chemistry, News Medical, Life Sciences and Medicine (last updated Oct. 27, 2013), [Retrieved from internet <URL: http://www.news-medical.net/health/Morphine-Chemistry.aspx >], 2 pages.*
Opioids, Bing images; internet <URL: http://i.imgur.com/9Zctous.png >, obtained Jul. 1, 2016.*
Christie et al., Cellular Actions of Opioids and other Analgesics: Implications for Synergism in Pain Relief, (1) Annual Scientific Meeting of ASCEPT, 1998: Symposium on Opiates and Pain; (2) Clinical and Experimental Pharmacology and Physiology (2000) 27: 520-523.*
Raffa et al., (Review Paper) Pharmacology of oral combination analgesics: rational therapy for pain, Journal of Clinical Pharmacy and Therapeutics (2001) 26: 257-264.*
Zhang et al., Signaling Cascades for δ-Opioid Receptor-Mediated Inhibition of GABA Synaptic Transmission and Behavioral Antinociception, Molecular Pharmacology (2012) 81: 375-383.*
Timothy J. Brennan et al., "Characterization of a Rat Model of Incisional Pain", Pain, 1996, pp. 493-501, vol. 64.
J.T. Litchfield, Jr. et al., "A Simplified Method of Evaluating Dose-Effect Experiments", 1948, pp. 99-113.
Lowell O. Randell et al., "A Method for Measurement of Analgesic Activity on Inflamed Tissue", Arch. Int. Pharmacodyn., 1957, pp. 409-419, CXI No. 4.
Ronald J. Tallarida et al., "Statistical Analysis of Drug-Drug and Site-Site Interactions with Isobolograms", Life Sciences, 1989, pp. 947-961, vol. 45, USA.
International Search Report dated Jul. 30, 2013 issued in PCT Application No. PCT/EP2013/001467 (five (5) pages).
Written Opinion (PCT/ISA/237) dated Jul. 30, 2013 issued in PCT Application No. PCT/EP2013/001467 (five (5) pages).
Schilling et al., "Acetaminophen: Old drug, new warnings," Cleveland Clinic Journal of Medicine, 2010, pp. 19-27, vol. 77, No. 1 (nine (9) pages).
International Search Report dated Jul. 30, 2013 issued in PCT Application No. PCT/EP2013/001470 (six (6) pages).
Written Opinion (PCT/ISA/237) dated Jul. 30, 2013 issued in PCT Application No. PCT/EP2013/001470 (five (5) pages).
International Search Report dated Jul. 30, 2013 issued in PCT Application No. PCT/EP2013/001468 (six (6) pages).
Written Opinion (PCT/ISA/237) dated Jul. 30, 2013 issued in PCT Application No. PCT/EP2013/001468 (five (5) pages).
International Search Report dated Jul. 30, 2013 issued in PCT Application No. PCT/EP2013/001469 (seven (7) pages).
Written Opinion (PCT/ISA/237) dated Jul. 30, 2013 issued in PCT Application No. PCT/EP2013/001469 (five (5) pages).
International Search Report dated Jul. 30, 2013 issued in PCT Application No. PCT/EP2013/001466 (six (6) pages).
Written Opinion (PCT/ISA/237) dated Jul. 30, 2013 issued in PCT Application No. PCT/EP2013/001466 (five (5) pages).
Larsen et al., "Design and application of prodrugs," 2002, pp. 410-458, Chapter 14 (twenty-five (25) pages).
Zelcer et al.,"Selective potentiation of opioid analgesia by nonsteroidal anti-inflammatory drugs," 2005, pp. 151-156, vol. 1040, Brain Research.
Co-pending U.S. Appl. No. 13/892,362, filed May 13, 2013.

* cited by examiner

PHARMACEUTICAL COMPOSITION COMPRISING (1R,4R)-6'-FLUORO-N,N-DI METHYL-4-PHENYL-4',9'-DIHYDRO-3'H-SPIRO[CYCLOHEXANE-1,1'-PYRANO-[3,4,B]INDOL]-4-AMINE AND A SALICYLIC ACID COMPONENT

The invention relates to a pharmaceutical composition comprising a first pharmacologically active ingredient selected from (1r,4r)-6'-fluoro-N,N-dimethyl-4-phenyl-4',9'-dihydro-3'H-spiro[cyclohexane-1,1'-pyrano[3,4,b]indol]-4-amine and the physiologically acceptable salts thereof, and a second pharmacologically active ingredient which is a salicylic acid component selected from the group consisting of acetylsalicylic acid, salicylic acid, salicylamide, ethenzamide, salsalate, dipyrocetyl, benorilate, diflunisal, guacetisal, and the physiologically acceptable salts thereof.

(1r,4r)-6'-fluoro-N,N-dimethyl-4-phenyl-4',9'-dihydro-3'H-spiro[cyclohexane-1,1'-pyrano[3,4,b]-indol]-4-amine and its corresponding physiologically acceptable salts as well as methods for their preparation are well known, for example, from WO2004/043967 and WO2008/040481.

The compounds exhibit analgesic properties and are particularly suitable for the treatment of acute, visceral, neuropathic or chronic (nociceptive) pain.

Salicylic acid and its derivatives are widely used as analgesic, anti-inflammatory and antipyretic drugs.

Though both of the aforementioned substance classes can be used in the prevention and treatment of pain and are as such therapeutically effective, side effects may occur, especially upon prolonged use or when administered at high dosages.

It is further known that specific combinations of pharmacologically active compounds exert supra-additive (synergistic) therapeutic effects upon administration. An advantage of these special cases is that the overall dose and accordingly the risk of undesired side effects may be reduced.

In a further aspect, two pharmacologically active compounds exerting a synergistic effect may be combined in one single pharmaceutical dosage form, e.g. a tablet, thus enhancing patient compliance.

It is an object of the invention to provide pharmaceutical compositions which have advantages compared to pharmaceutical compositions of the prior art. In particular, the pharmaceutical compositions should provide rapid therapeutic effects, but also should have a high tolerability, good compliance and safety.

This object has been achieved by the subject-matter of the patent claims.

It has been surprisingly found that a pharmaceutical composition comprising (1r,4r)-6'-fluoro-N,N-dimethyl-4-phenyl-4',9'-dihydro-3'H-spiro[cyclohexane-1,1'-pyrano[3,4,b]indol]-4-amine and a salicyclic acid component, such as acetylsalicylic acid, is useful for the treatment of acute and chronic pain.

Further it has been surprisingly found that said pharmaceutical composition exhibits a synergistic therapeutic effect upon administration. Therefore, the overall administered dose may be lowered, so that fewer undesired side-effects will occur.

A first aspect of the invention relates to a pharmaceutical composition comprising:
(a) a first pharmacologically active ingredient selected from (1r,4r)-6'-fluoro-N,N-dimethyl-4-phenyl-4',9'-dihydro-3'H-spiro[cyclohexane-1,1'-pyrano[3,4,b]indol]-4-amine and the physiologically acceptable salts thereof, and
(b) a second pharmacologically active ingredient which is a salicylic acid component selected from the group consisting of acetylsalicylic acid, salicylic acid, salicylamide, ethenzamide, salsalate, dipyrocetyl, benorilate, diflunisal, guacetisal, and the physiologically acceptable salts thereof.

The pharmaceutical composition according to the invention comprises a first pharmacologically active ingredient selected from (1r,4r)-6'-fluoro-N,N-dimethyl-4-phenyl-4',9'-dihydro-3'H-spiro[cyclohexane-1,1'-pyrano[3,4,b]indol]-4-amine and the physiologically acceptable salts thereof.

For the purpose of specification, (1r,4r)-6'-fluoro-N,N-dimethyl-4-phenyl-4',9'-dihydro-3'H-spiro[cyclohexane-1,1'-pyrano[3,4,b]indol]-4-amine is the compound according to formula (I) which can also be referred to as 1,1-(3-dimethylamino-3-phenylpentamethylene)-6-fluoro-1,3,4,9-tetrahydropyrano[3,4-b]indole (trans)

(I)

The definition of the first pharmacologically active ingredient includes (1r,4r)-6'-fluoro-N,N-dimethyl-4-phenyl-4',9'-dihydro-3'H-spiro[cyclohexane-1,1'-pyrano-[3,4,b]indol]-4-amine in form of the free base, i.e. the compound according to formula (I), in any possible form including solvates, cocrystals and polymorphs, and its physiologically acceptable salts, in particular acid addition salts and corresponding solvates, cocrystals and polymorphs.

The pharmacologically active ingredient (1r,4r)-6'-fluoro-N,N-dimethyl-4-phenyl-4',9'-dihydro-3'H-spiro[cyclohexane-1,1'-pyrano[3,4,b]indol]-4-amine may be present in the pharmaceutical composition according to the invention in form of a physiologically acceptable salt, preferably an acid addition salt, whereby any suitable acid capable of forming such an addition salt may be used.

The conversion of (1r,4r)-6'-fluoro-N,N-dimethyl-4-phenyl-4',9'-dihydro-3'H-spiro[cyclohexane-1,1'-pyrano[3,4,b]indol]-4-amine into a corresponding addition salt, for example, via reaction with a suitable acid may be effected in a manner well known to those skilled in the art. Suitable acids include but are not limited to hydrochloric acid, hydrobromic acid, sulfuric acid, methanesulfonic acid, formic acid, acetic acid, oxalic acid, succinic acid, tartaric acid, mandelic acid, fumaric acid, lactic acid, citric acid, glutamic acid and/or aspartic acid. Salt formation is preferably effected in a solvent, for example, diethyl ether, diisopropyl ether, alkyl acetates, acetone and/or 2-butanone. Moreover, trimethylchlorosilane in aqueous solution is also suitable for the preparation of hydrochlorides.

In a preferred embodiment, the first pharmacologically active ingredient is (1r,4r)-6'-fluoro-N,N-dimethyl-4-phenyl-4',9'-dihydro-3'H-spiro[cyclohexane-1,1'-pyrano[3,4,b]indol]-4-amine in form of the free base, i.e. the compound according to formula (I).

In another preferred embodiment, the first pharmacologically active ingredient is (1r,4r)-6'-fluoro-N,N-dimethyl-4-phenyl-4',9'-dihydro-3'H-spiro[cyclohexane-1,1'-pyrano[3,4,b]indol]-4-amine in form of a physiologically acceptable acid addition salt, in particular the hydrochloride, hemicitrate or maleate salt.

Unless explicitly stated otherwise, all amounts of the first pharmacologically active ingredient specified in the following are given according to the corresponding amount of (1r,4r)-6'-fluoro-N,N-dimethyl-4-phenyl-4',9'-dihydro-3'H-spiro[cyclohexane-1,1'-pyrano[3,4,b]indol]-4-amine in form of the free base, i.e. the compound according to formula (I).

The pharmaceutical composition according to the invention comprises a second pharmacologically active ingredient which is a salicylic acid component selected from the group consisting of acetylsalicylic acid, salicylic acid, salicylamide, ethenzamide, salsalate, dipyrocetyl, benorilate, diflunisal, guacetisal, and the physiologically acceptable salts thereof.

The definition of the second pharmacologically active ingredient includes the aforementioned salicylic acid components in any possible form including solvates, cocrystals and polymorphs, and their physiologically acceptable salts, in particular metal salts, quaternary ammonium salts; N-heteroarylium salts and amino acid salts, and corresponding solvates, cocrystals and polymorphs.

Acetylsalicylic acid, salicylic acid, salsalate, dipyrocetyl, and diflunisal contain a free carboxylic acid group and may be converted into a corresponding salt, in particular metal salts, quaternary ammonium salt; N-heteroarylium salt or amino acid salt, in a manner well known to those skilled in the art, for example, via reaction with a suitable base or amino acid. Suitable bases include but are not limited to inorganic bases, including the hydroxides of sodium, potassium, calcium, magnesium, aluminium and zinc; and organic bases, such as triethyl amine, trimethylamine, N,N-diisopropylethylamine, N-methylmorpholine, morpholine, N-methylpiperidine, imidazole and ammonia. As suitable amino acid, lysine may be used. Salt formation is preferably effected in a solvent, for example, diethyl ether, diisopropyl ether, alkyl acetates, acetone and/or 2-butanone.

In a preferred embodiment, the second pharmacologically active ingredient is selected from the group consisting of acetylsalicylic acid, salicylic acid, salsalate, dipyrocetyl, diflunisal, and the physiologically acceptable salts thereof; in particular metals salts, including sodium, potassium, magnesium, calcium aluminium and zinc salts; quaternary ammonium salts, e.g. derived from morpholine or choline, N-heteroarylium salts, e.g. derived from imidazole; and amino acid salts thereof.

In another preferred embodiment, the second pharmacologically active ingredient is selected from salicylamide and ethenzamide, and the physiologically acceptable salts thereof.

Unless explicitly stated otherwise, all amounts of the second pharmacologically active ingredient specified in the following are given according to the corresponding amount of the free carboxylic acid.

In an especially preferred embodiment, the second pharmacologically active ingredient is selected from acetylsalicyclic acid and the physiologically acceptable salts, in particular metals salts, including sodium, potassium, magnesium, calcium aluminium and zinc salts; quaternary ammonium salts, e.g. derived from morpholine or choline, N-heteroarylium salts, e.g. derived from imidazole; and amino acid salts thereof; aluminium-bis(acetylsalicylat)-hydroxid, calcium-bis(O-acetylsalicylat) and lysin-acetylsalicylat are especially preferred.

In a preferred embodiment, the first pharmacologically active ingredient is (1r,4r)-6'-fluoro-N,N-dimethyl-4-phenyl-4',9'-dihydro-3'H-spiro[cyclohexane-1,1'-pyrano[3,4,b]indol]-4-amine in form of the free base, i.e. the compound according to formula (I), and the second pharmacologically active ingredient is selected from the group consisting of acetylsalicylic acid, salicylic acid, salsalate, dipyrocetyl, and diflunisal, and the physiologically acceptable salts thereof.

In another preferred embodiment, the first pharmacologically active ingredient is (1r,4r)-6'-fluoro-N,N-dimethyl-4-phenyl-4',9'-dihydro-3'H-spiro[cyclohexane-1,1'-pyrano[3,4,b]indol]-4-amine in form of a physiologically acceptable acid addition salt, in particular the hydrochloride, hemicitrate or maleate salt, and the second pharmacologically active ingredient is selected from the group consisting of acetylsalicylic acid, salicylic acid, salsalate, dipyrocetyl, and diflunisal, and the physiologically acceptable salts thereof.

In a preferred embodiment, the first pharmacologically active ingredient is (1r,4r)-6'-fluoro-N,N-dimethyl-4-phenyl-4',9'-dihydro-3'H-spiro[cyclohexane-1,1'-pyrano[3,4,b]indol]-4-amine in form of the free base, i.e. the compound according to formula (I), and the second pharmacologically active ingredient is selected from acetylsalicylic acid and the physiologically acceptable salts thereof.

In another preferred embodiment, the first pharmacologically active ingredient is (1r,4r)-6'-fluoro-N,N-dimethyl-4-phenyl-4',9'-dihydro-3'H-spiro[cyclohexane-1,1'-pyrano[3,4,b]indol]-4-amine in form of a physiologically acceptable acid addition salt, in particular the hydrochloride, hemicitrate or maleate salt, and the second pharmacologically active ingredient is selected from acetylsalicylic acid and the physiologically acceptable salts thereof.

In a further preferred embodiment, the first pharmacologically active ingredient is (1r,4r)-6'-fluoro-N,N-dimethyl-4-phenyl-4',9'-dihydro-3'H-spiro[cyclohexane-1,1'-pyrano[3,4,b]indol]-4-amine in form of the free base, i.e. the compound according to formula (I), and the second pharmacologically active ingredient is acetylsalicylic acid.

In a still further preferred embodiment, the first pharmacologically active ingredient is (1r,4r)-6'-fluoro-N,N-dimethyl-4-phenyl-4',9'-dihydro-3'H-spiro[cyclohexane-1,1'-pyrano[3,4,b]indol]-4-amine in form of a physiologically acceptable acid addition salt, in particular the hydrochloride, hemicitrate or maleate salt, and the second pharmacologically active ingredient is acetylsalicylic acid.

In a preferred embodiment, the first pharmacologically active ingredient is (1r,4r)-6'-fluoro-N,N-dimethyl-4-phenyl-4',9'-dihydro-3'H-spiro[cyclohexane-1,1'-pyrano[3,4,b]indol]-4-amine in form of the free base, i.e. the compound according to formula (I), and the second pharmacologically active ingredient is acetylsalicylic acid in form of a physiologically acceptable salt, preferably metal salt, quaternary ammonium salt, N-heteroarylium salt or amino acid salt.

In another preferred embodiment, the first pharmacologically active ingredient is (1r,4r)-6'-fluoro-N,N-dimethyl-4-phenyl-4',9'-dihydro-3'H-spiro[cyclohexane-1,1'-pyrano[3,4,b]indol]-4-amine in form of a physiologically acceptable acid addition salt, in particular the hydrochloride, hemicitrate or maleate salt, and the second pharmacologically active ingredient is acetylsalicylic acid in form of a physiologically acceptable salt, preferably metal salt, quaternary ammonium salt, N-heteroarylium salt or amino acid salt.

In case that the second pharmacologically active ingredient contains a carboxyl group, it may react with the first pharmacologically active ingredient according to formula (I) forming a salt which incorporates both pharmacologically active ingredients.

Thus, in another preferred embodiment, the pharmaceutical composition according to the invention comprises the first and the second pharmacologically active ingredient in form of a salt formed from these two pharmacologically active ingredients. Such a salt formation may be partial, i.e. the pharmaceutical composition according to the invention comprises one or both of these pharmacologically active ingredients also in their non-salt form, or the salt formation may essentially be complete.

Another aspect of the invention relates to a pharmaceutical dosage form comprising the pharmaceutical composition according to the invention.

The first and the second pharmacologically active ingredient are typically contained in the pharmaceutical dosage form according to the invention in a therapeutically effective amount. The amount that constitutes a therapeutically effective amount varies according to the pharmacologically active ingredients, the condition being treated, the severity of said condition, the patient being treated, and whether the pharmaceutical dosage form is designed for an immediate or controlled release.

In a preferred embodiment, the content of the first pharmacologically active ingredient in the pharmaceutical dosage form according to the invention and the pharmaceutical composition according to the invention, respectively, is at most 10 wt.-% or at most 5 wt.-% or at most 3 wt.-% or at most 1.0 wt.-%, more preferably at most 0.8 wt.-%, yet more preferably at most 0.5 wt.-%, still more preferably at most 0.2 wt.-%, even more preferably at most 0.1 wt.-%, most preferably at most 0.05 wt.-%, and in particular at most 0.01 wt.-% or at most 0.005 wt.-% or at most 0.001 wt.-%.

In a preferred embodiment, the content of the second pharmacologically active ingredient in the pharmaceutical dosage form according to the invention and the pharmaceutical composition according to the invention, respectively, is at most 95 wt.-%, more preferably at most 80 wt.-%, yet more preferably at most 70 wt.-%, still more preferably at most 60 wt.-%, even more preferably at most 55 wt.-%, most preferably at most 50 wt.-%, and in particular at most 45 wt.-%.

In a preferred embodiment, the content of the first pharmacologically active ingredient in the pharmaceutical dosage form according to the invention and the pharmaceutical composition according to the invention, respectively, is at least 0.0001 wt.-%, more preferably at least 0.0003 wt.-%, yet more preferably at least 0.0005 wt.-%, still more preferably at least 0.0008 wt.-%, even more preferably at least 0.001 wt.-%, most preferably at least 0.003 wt.-%, and in particular at least 0.005 wt.-%.

In a preferred embodiment, the content of the second pharmacologically active ingredient in the pharmaceutical dosage form according to the invention and the pharmaceutical composition according to the invention, respectively, is at least 0.1 wt.-%, more preferably at least 0.5 wt.-%, yet more preferably at least 1 wt.-%, still more preferably at least 3 wt.-%, even more preferably at least 5 wt.-%, most preferably at least 7.5 wt.-%, and in particular at least 10 wt.-%.

Unless explicitly stated otherwise, in the meaning of the invention the indication "wt.-%" shall mean weight of the respective ingredient per total weight of the pharmaceutical dosage form or per total weight of the pharmaceutical composition, respectively.

Preferably, in the pharmaceutical dosage form according to the invention and the pharmaceutical composition according to the invention, respectively, the relative weight ratio of the first pharmacologically active ingredient to the second pharmacologically active ingredient is within the range of from 1:2 to 1:1,000,000, more preferably 1:30 to 1:1,000,000, most preferably 1:500 to 1:500,000, and in particular 1:1,000 to 1:250,000.

In a preferred embodiment, in the pharmaceutical dosage form according to the invention and the pharmaceutical composition according to the invention, respectively, the relative weight ratio of the first pharmacologically active ingredient to the second pharmacologically active ingredient is within the range of from 1:100 to 1:10,000, more preferably 1:200 to 1:7,500, still more preferably 1:500 to 1:5,000, most preferably 1:750 to 1:2,500, and in particular 1:900 to 1:2,000.

In another preferred embodiment, in the pharmaceutical dosage form according to the invention and the pharmaceutical composition according to the invention, respectively, the relative weight ratio of the first pharmacologically active ingredient to the second pharmacologically active ingredient is within the range of from 1:500 to 1:50,000, more preferably 1:1,000 to 1:20,000, still more preferably 1:2,000 to 1:10,000, most preferably 1:3,000 to 1:8,000, and in particular 1:4,000 to 1:6,000.

In yet another preferred embodiment, in the pharmaceutical dosage form according to the invention and the pharmaceutical composition according to the invention, respectively, the relative weight ratio of the first pharmacologically active ingredient to the second pharmacologically active ingredient is within the range of from 1:1,000 to 1:50,000, more preferably 1:2,000 to 1:25,000, still more preferably 1:3,000 to 1:18,000, yet more preferably 1:4,000 to 1:15,000, most preferably 1:5,000 to 1:12,000, and in particular 1:6,000 to 1:9,000.

In a further preferred embodiment, in the pharmaceutical dosage form according to the invention and the pharmaceutical composition according to the invention, respectively, the relative weight ratio of the first pharmacologically active ingredient to the second pharmacologically active ingredient is within the range of from 1:1,000 to 1:100,000, more preferably 1:2,000 to 1:80,000, still more preferably 1:4,000 to 1:50,000, yet more preferably 1:6,000 to 1:20,000, most preferably 1:8,000 to 1:15,000, and in particular 1:9,000 to 1:12,500.

In a still further preferred embodiment, in the pharmaceutical dosage form according to the invention and the pharmaceutical composition according to the invention, respectively, the relative weight ratio of the first pharmacologically active ingredient to the second pharmacologically active ingredient is within the range of from 1:5,000 to 1:500,000, more preferably 1:10,000 to 1:250,000, still more preferably 1:20,000 to 1:150,000, most preferably 1:40,000 to 1:120,000, and in particular 1:50,000 to 1:100,000.

Preferably, in the pharmaceutical dosage form according to the invention and the pharmaceutical composition according to the invention, respectively, the relative molar ratio of the first pharmacologically active ingredient to the second pharmacologically active ingredient is within the range of from 1:100 to 1:1,000,000, more preferably 1:500 to 1:500,000, and most preferably 1:1,000 to 1:250,000.

In a preferred embodiment, in the pharmaceutical dosage form according to the invention and the pharmaceutical composition according to the invention, respectively, the relative molar ratio of the first pharmacologically active ingredient to the second pharmacologically active ingredient is within the range of from 1:2 to 1:1,000,000, more preferably 1:30 to 1:1,000,000, even more preferably 1:100 to 1:10,000, still more preferably 1:200 to 1:7,500, yet more preferably 1:500 to 1:5,000, most preferably 1:750 to 1:2,500, and in particular 1:900 to 1:2,000.

In another preferred embodiment, in the pharmaceutical dosage form according to the invention and the pharmaceutical composition according to the invention, respectively, the relative molar ratio of the first pharmacologically active ingredient to the second pharmacologically active ingredient is within the range of from 1:500 to 1:50,000, more preferably 1:1,000 to 1:20,000, still more preferably 1:2,000 to 1:10,000, most preferably 1:3,000 to 1:8,000, and in particular 1:4,000 to 1:6,000.

In yet another preferred embodiment, in the pharmaceutical dosage form according to the invention and the pharmaceutical composition according to the invention, respectively, the relative molar ratio of the first pharmacologically active ingredient to the second pharmacologically active ingredient is within the range of from 1:1,000 to 1:50,000, more preferably 1:2,000 to 1:25,000, still more preferably 1:3,000 to 1:18,000, yet more preferably 1:4,000 to 1:15,000, most preferably 1:5,000 to 1:12,000, and in particular 1:6,000 to 1:9,000.

In a further preferred embodiment, in the pharmaceutical dosage form according to the invention and the pharmaceutical composition according to the invention, respectively, the relative molar ratio of the first pharmacologically active ingredient to the second pharmacologically active ingredient is within the range of from 1:1,000 to 1:100,000, more preferably 1:2,000 to 1:80,000, still more preferably 1:4,000 to 1:50,000, yet more preferably 1:6,000 to 1:20,000, most preferably 1:8,000 to 1:15,000, and in particular 1:9,000 to 1:12,500.

In a still further preferred embodiment, in the pharmaceutical dosage form according to the invention and the pharmaceutical composition according to the invention, respectively, the relative molar ratio of the first pharmacologically active ingredient to the second pharmacologically active ingredient is within the range of from 1:5,000 to 1:500,000, more preferably 1:10,000 to 1:250,000, still more preferably 1:20,000 to 1:150,000, most preferably 1:40,000 to 1:120,000, and in particular 1:50,000 to 1:100,000.

The amounts of the first and the second pharmacologically active ingredient contained in the pharmaceutical dosage form according to the invention may vary depending on different factors well known to those skilled in the art, for example, the weight of the patient, the route of administration, the severity of the illness and the like.

In general, both pharmacologically active ingredients contained in the pharmaceutical dosage form according to the invention may be administered in amounts up to their maximum daily dose, which is known to those skilled in the art. For example, as the second pharmacologically active ingredient, acetylsalicylic acid may preferably be administered to a patient in a maximum daily dose of up to 4,000 mg; diflunisal may preferably be administered to a patient in a maximum daily dose of up to 1,500 mg, and salsalate may preferably be administered to a patient in a maximum daily dose of up to 4,000 mg.

When administered in the prescribed manner, e.g. once daily or twice daily, the pharmaceutical dosage form according to the invention and the pharmaceutical composition according to the invention, respectively, preferably contain the first and the second pharmacologically active ingredient, independently of one another, in an amount corresponding to 75±15 wt.-%, 75±10 wt.-%, 75±5 wt.-%, 50±15 wt.-%, 50±10 wt.-%, 50±5 wt.-%, 25±15 wt.-%, 25±10 wt.-% or 25±5 wt.-% of the respective maximum daily dose of the first and the second pharmacologically active ingredient, respectively.

Preferably, the pharmaceutical dosage form according to the invention contains the first pharmacologically active ingredient in a dose of from 0.1 µg to 5,000 µg, more preferably, 0.1 µg to 2,500 µg, still more preferably 1.0 µg to 1,000 µg, yet more preferably 10 to 800 µg, most preferably 15 µg to 600 µg, and in particular 20 µg to 440 µg.

In a preferred embodiment, the pharmaceutical dosage form according to the invention contains the first pharmacologically active ingredient in a dose within the range of 13±12 µg, more preferably 13±10 µg, still more preferably 13±8 µg, yet more preferably 13±6 µg, even more preferably 13±5 µg, most preferably 13±4 µg, and in particular 13±3 µg.

In another preferred embodiment, the pharmaceutical dosage form according to the invention contains the first pharmacologically active ingredient in a dose within the range of 20±15 µg, more preferably 20±13 µg, still more preferably 20±12 µg, yet more preferably 20±10 µg, even more preferably 20±8 µg, most preferably 20±6 µg, and in particular 20±5 µg.

In still another preferred embodiment, the pharmaceutical dosage form according to the invention contains the first pharmacologically active ingredient in a dose within the range of 40±35 µg, more preferably 40±30 µg, still more preferably 40±25 µg, yet more preferably 40±20 µg, even more preferably 40±15 µg, most preferably 40±10 µg, and in particular 40±5 µg.

In yet another preferred embodiment, the pharmaceutical dosage form according to the invention contains the first pharmacologically active ingredient in a dose within the range of 60±50 µg, more preferably 60±40 µg, still more preferably 60±30 µg, yet more preferably 60±20 µg, most preferably 60±10 µg, and in particular 60±5 µg.

In a further preferred embodiment, the pharmaceutical dosage form according to the invention contains the first pharmacologically active ingredient in a dose within the range of 80±70 µg, more preferably 80±60 µg, still more preferably 80±50 µg, yet more preferably 80±40 µg, even more preferably 80±20 µg, most preferably 80±10 µg, and in particular 80±5 µg.

In still a further preferred embodiment, the pharmaceutical dosage form according to the invention contains the first pharmacologically active ingredient in a dose within the range of 100±90 µg, more preferably 100±80 µg, still more preferably 100±60 µg, yet more preferably 100±40 µg, even more preferably 100±20 µg, most preferably 100±10 µg, and in particular 100±5 µg.

In yet a further preferred embodiment, the pharmaceutical dosage form according to the invention contains the first pharmacologically active ingredient in a dose within the range of 120±100 µg, more preferably 120±80 µg, still more preferably 120±60 µg, yet more preferably 120±40 µg, even more preferably 120±20 µg, most preferably 120±10 µg, and in particular 120±5 µg.

In another preferred embodiment, the pharmaceutical dosage form according to the invention contains the first pharmacologically active ingredient in a dose within the range of 150±90 µg, more preferably 150±80 µg, still more preferably 150±60 µg, yet more preferably 150±40 µg, even more preferably 150±20 µg, most preferably 150±10 µg, and in particular 150±5 µg.

In still another preferred embodiment, the pharmaceutical dosage form according to the invention contains the first pharmacologically active ingredient in a dose within the range of 170±130 µg, more preferably 170±100 µg, still more preferably 170±80 µg, yet more preferably 170±60 µg, even more preferably 170±40 µg, most preferably 170±20 µg, and in particular 170±10 µg.

In yet another preferred embodiment, the pharmaceutical dosage form according to the invention contains the first pharmacologically active ingredient in a dose within the range of 200±175 µg, more preferably 200±150 µg, still more preferably 200±125 µg, yet more preferably 200±100 µg, even more preferably 200±75 µg, most preferably 200±50 µg, and in particular 200±25 µg.

In a further preferred embodiment, the pharmaceutical dosage form according to the invention contains the first pharmacologically active ingredient in a dose within the range of 400±350 µg, more preferably 400±300 µg, still more preferably 400±250 µg, yet more preferably 400±200 µg, even more preferably 400±150 µg, most preferably 400±100 µg, and in particular 400±50 µg.

In another preferred embodiment, the pharmaceutical dosage form according to the invention contains the first pharmacologically active ingredient in a dose within the range of 600±400 µg, more preferably 600±300 µg, still more preferably 600±250 µg, yet more preferably 600±200 µg, even more preferably 600±150 µg, most preferably 600±100 µg, and in particular 600±50 µg.

In still another preferred embodiment, the pharmaceutical dosage form according to the invention contains the first pharmacologically active ingredient in a dose within the range of 800±550 µg, more preferably 800±400 µg, still more preferably 800±350 µg, yet more preferably 800±250 µg, even more preferably 800±150 µg, most preferably 800±100 µg, and in particular 800±50 µg.

In yet another preferred embodiment, the pharmaceutical dosage form according to the invention contains the first pharmacologically active ingredient in a dose within the range of 1,000±800 µg, more preferably 1,000±600 µg, still more preferably 1,000±500 µg, yet more preferably 1,000±300 µg, even more preferably 1,000±200 µg, most preferably 1,000±100 µg, and in particular 1,000±50 µg.

In a further preferred embodiment, the pharmaceutical dosage form according to the invention contains the first pharmacologically active ingredient in a dose within the range of 1,200±1,000 µg, more preferably 1,200±800 µg, still more preferably 1,200±600 µg, yet more preferably 1,200±400 µg, even more preferably 1,200±200 µg, most preferably 1,200±100 µg, and in particular 1,200±50 µg.

Preferably, the pharmaceutical dosage form according to the invention contains the second pharmacologically active ingredient in a dose of from 10 mg to 7,500 mg, more preferably 50 mg to 5,000 mg, most preferably 50 to 4,000 mg, and in particular 100 to 3,000 mg.

In a preferred embodiment, the pharmaceutical dosage form according to the invention contains the second pharmacologically active ingredient in a dose within the range of 100±90 mg, more preferably 100±75 mg, still more preferably 100±50 mg, yet more preferably 100±40 mg, even more preferably 100±30 mg, most preferably 100±20 mg, and in particular 100±10 mg.

In another preferred embodiment, the pharmaceutical dosage form according to the invention contains the second pharmacologically active ingredient in a dose within the range of 200±150 mg, more preferably 200±100 mg, still more preferably 200±75 mg, yet more preferably 200±50 mg, even more preferably 200±35 mg, most preferably 200±20 mg, and in particular 200±10 mg.

In still another preferred embodiment, the pharmaceutical dosage form according to the invention contains the second pharmacologically active ingredient in a dose within the range of 300±150 mg, more preferably 300±100 mg, still more preferably 300±75 mg, yet more preferably 300±50 mg, even more preferably 300±35 mg, most preferably 300±20 mg, and in particular 300±10 mg.

In yet another preferred embodiment, the pharmaceutical dosage form according to the invention contains the second pharmacologically active ingredient in a dose within the range of 500±400 mg, more preferably 500±300 mg, still more preferably 500±200 mg, yet more preferably 500±150 mg, even more preferably 500±100 mg, most preferably 500±75 mg, and in particular 500±50 mg.

In a further preferred embodiment, the pharmaceutical dosage form according to the invention contains the second pharmacologically active ingredient in a dose within the range of 1,000±800 mg, more preferably 1,000±600 mg, still more preferably 1,000±400 mg, yet more preferably 1,000±200 mg, even more preferably 1,000±150 mg, most preferably 1,000±100 mg, and in particular 1,000±50 mg.

In a still further preferred embodiment, the pharmaceutical dosage form according to the invention contains the second pharmacologically active ingredient in a dose within the range of 1,500±1,000 mg, more preferably 1,500±800 mg, still more preferably 1,500±500 mg, yet more preferably 1,500±400 mg, even more preferably 1,500±300 mg, most preferably 1,500±200 mg, and in particular 1,500±100 mg.

In a preferred embodiment, the pharmaceutical dosage form contains acetylsalicylic acid or a physiologically acceptable salt thereof as the second pharmacologically active ingredient in a dose within the range of 10 mg to 2,000 mg, more preferably in the range of 25 mg to 1,500 mg, even more preferably in the range of 50 mg to 1,000 mg, most preferably in the range of 100 mg to 750 mg, and in particular in the range of 100 mg to 500 mg.

In another preferred embodiment, the pharmaceutical dosage form contains acetylsalicylic acid or a physiologically acceptable salt thereof as the second pharmacologically active ingredient in a dose within the range of 50 mg to 4,000 mg, more preferably in the range of 100 mg to 3,000 mg, even more preferably in the range of 200 mg to 2,000 mg, most preferably in the range of 250 mg to 1,750 mg, and in particular in the range of 300 mg to 1,500 mg.

In the pharmaceutical dosage form according to the invention, the dose of the first pharmacologically active ingredient is preferably within the range of from 1:20 to 20:1 of the amount which is equieffective to the dosage of the second pharmacologically active ingredient. In this regard, "equieffective" preferably means the dosage that would be required in order to achieve the equivalent desired therapeutic effect when being administered alone. A skilled person recognizes that when the desired therapeutic effect is an analgesic effect, the equieffective dosage is determined with respect to the analgesic properties of the first pharmacologically active ingredient and the second pharmacological ingredient.

For example, when the dose of the second pharmacologically active ingredient, which is contained in the pharmaceutical dosage form according to the invention, amounts to e.g. 30 mg and provides an analgesic effect E when being administered alone at this dose, and when the equieffective amount of the first pharmacologically active ingredient, i.e. the amount needed in order to provide the same analgesic effect E when being administered alone, would be e.g. 4 µg, the dosage of the first pharmacologically active ingredient, which is contained in the pharmaceutical dosage form according to the invention, may vary from 0.2 µg (4 µg/20) to 80 µg (20.4 µg).

In a preferred embodiment, the dose of the first pharmacologically active ingredient is within the range of from 1:15 to 15:1, preferably within the range of from 1:10 to 10:1, more preferably within the range of from 1:8 to 8:1, still more preferably within the range of from 1:6 to 6:1, yet more preferably within the range of from 1:4 to 4:1, most preferably within the range of from 1:3 to 3:1, and in particular preferably within the range of from 1:2 to 2:1, of the amount which is equieffective to the dose of the second pharmacologically active ingredient.

Suitable pathways of administration of the pharmaceutical dosage form according to the invention include but are not limited to oral, intravenous, intraperitoneal, intradermal, transdermal, intrathecal, intramuscular, intranasal, transmucosal, subcutaneous, local and/or rectal administration.

In a preferred embodiment, the pharmaceutical dosage form according to the invention is for oral administration.

In another preferred embodiment, the pharmaceutical dosage form according to the invention is for parenteral administration; in particular intravenous, intraperitoneal, intrathecal, intramuscular, or subcutaneous administration.

In still another preferred embodiment, the pharmaceutical dosage form according to the invention is for rectal administration.

The pharmaceutical dosage form according to the invention and the pharmaceutical composition according to the invention, respectively, can be solid, semi-solid or liquid.

The pharmaceutical dosage form according to the invention and the pharmaceutical composition according to the invention, respectively, may contain auxiliary agents, for example, carriers, fillers, solvents, diluents, colorants and/or binders. The selection of auxiliary agents and of the amounts of the same to be used depends, for example, on how the first and the second pharmacologically active ingredient are to be administered, e.g. orally, intravenously, intraperitoneally, intradermally, transdermally, intrathecally, intramuscularly, intranasally, transmucosally, subcutaneously, rectally or locally.

Suitable auxiliary agents are in particular any substances known to a person skilled in the art useful for the preparation of galenical dosage forms. Examples of suitable auxiliary agents include but are not limited to: water, ethanol, 2-propanol, glycerol, ethylene glycol, propylene glycol, polyethylene glycol, polypropylene glycol, glucose, fructose, lactose, saccharose, dextrose, molasses, starch, modified starch, gelatine, sorbitol, inositol, mannitol, microcrystalline cellulose, methyl cellulose, carboxymethyl cellulose, cellulose acetate, shellac, cetyl alcohol, polyvinyl pyrrolidone, paraffins, waxes, natural and synthetic gums, acacia gum, alginates, dextran, saturated and unsaturated fatty acids, stearic acid, magnesium stearate, zinc stearate, glycerol stearate, sodium lauryl sulphate, edible oils, sesame oil, coconut oil, peanut oil, soybean oil, lecithin, sodium lactate, polyoxyethylene and polypropylene fatty acid ester, sorbitan fatty acid ester, sorbic acid, benzoic acid, citric acid, ascorbic acid, tannic acid, sodium chloride, potassium chloride, magnesium chloride, calcium chloride, magnesium oxide, zinc oxide, silicon dioxide, titanium oxide, titanium dioxide, magnesium sulphate, zinc sulphate, calcium sulphate, potash, calcium phosphate, dicalcium phosphate, potassium bromide, potassium iodide, talcum, kaolin, pectin, crosspovidone, agar and bentonite.

Pharmaceutical dosage forms which are suitable for oral administration include but are not limited to tablets, effervescent tablets, chewing tablets, dragees, capsules, drops, juices and syrups. Oral pharmaceutical dosage forms may also be in the form of multiparticulates such as granules, pellets, spheres, crystals and the like, optionally compressed into a tablet, filled into a capsule, filled into a sachet or suspended in a suitable liquid medium. Oral pharmaceutical dosage forms may also be equipped with an enteric coating.

Pharmaceutical dosage forms that are suitable for parenteral, topical and inhalative administration include but are not limited to solutions, suspensions, easily reconstitutable dry preparations and sprays.

Suppositories are a suitable pharmaceutical dosage form for rectal administration. Dosage forms in a deposit, in dissolved form, for example, in a patch optionally with the addition of agents to promote skin penetration, are examples of suitable dosage forms for percutaneous administration.

In a preferred embodiment, the pharmaceutical dosage form according to the invention is a tablet.

In a preferred embodiment, the pharmaceutical dosage form according to the invention is for administration six times daily, five times daily, four times daily, thrice daily, twice daily, once daily, or less frequently.

In a preferred embodiment, the pharmaceutical dosage form according to the invention is for administration once daily.

In another preferred embodiment, the pharmaceutical dosage form according to the invention is for administration multiple daily, in particular twice daily, thrice daily, or up to six times a day.

In a preferred embodiment, the pharmaceutical dosage form according to the invention is for administration twice daily.

In another preferred embodiment, the pharmaceutical dosage form according to the invention is for administration thrice daily.

For the purpose of specification, "administration thrice daily" (tid) preferably means that the pharmaceutical dosage form according to the invention is adapted for being consecutively administered according to a regimen comprising the administration of three pharmaceutical dosage forms per day, wherein the time interval between the consecutive administration of two pharmaceutical dosage forms is at least 3 hours, preferably at least 4 hours, more preferably not least 6 hours and in particular, about 8 hours.

For the purpose of specification, "administration twice daily" (bid) preferably means that the pharmaceutical dosage form according to the invention is adapted for being consecutively administered according to a regimen comprising the administration of two pharmaceutical dosage forms per day, wherein the time interval between the consecutive administration of two pharmaceutical dosage forms is at least 6 hours, preferably at least 8 hours, more preferably at least 10 hours and in particular, about 12 hours.

For the purpose of specification, "administration once daily" (sid) preferably means that the pharmaceutical dosage form according to the invention is adapted for being consecutively administered according to a regimen comprising the administration of one pharmaceutical dosage form per day, wherein the time interval between the consecutive administration of two pharmaceutical dosage forms is at least 18 hours, preferably at least 20 hours, more preferably at least 22 hours and in particular, about 24 hours.

A skilled person is fully aware that the above administration regimens may be realized by administering a single pharmaceutical dosage form containing the full amount of the first pharmacologically active ingredient and the full amount of the second pharmacologically active ingredient to be administered at a particular point in time or, alternatively, administering a multitude of dose units, i.e. two, three or more dose units, the sum of which multitude of dose units containing the full amount of the first pharmacologically active ingredient and the second pharmacologically active ingredient to be administered at said particular point in time, where the individual dose units are adapted for simultaneous administration or administration within a short period of time, e.g. within 5, 10 or 15 minutes.

In the following, the doses of the first and the second pharmacologically active ingredient are expressed according to the number of prescribed administrations "n" per day, i.e. the number of administrations of the pharmaceutical dosage form according to the invention in the course of 24 hours. As an example, 100/n µg in case of an administration once daily (n=1) corresponds to a dose of 100 µg, and 100/n µg in case of an administration twice daily (n=2) corresponds to a dose of 50 µg.

In a preferred embodiment, the pharmaceutical dosage form according to the invention is for administration once daily (n=1), wherein the pharmaceutical dosage form contains the first pharmacologically active ingredient in a dose of from 15/n to 100/n µg, preferably 20/n to 80/n µg, and the second pharmacologically active ingredient in a dose of from 100/n to 3,000/n mg. According to this embodiment, the pharmaceutical dosage form according to the invention is preferably for oral administration, preferably in form of a tablet.

In another preferred embodiment, the pharmaceutical dosage form according to the invention is for administration multiple daily (n=2, 3, 4, 5 or 6), wherein the pharmaceutical dosage form contains the first pharmacologically active ingredient in a dose of from 15/n to 100/n µg, preferably 20/n to 80/n µg, and the second pharmacologically active ingredient in a dose of from 100/n to 3,000/n mg. According to this embodiment, the pharmaceutical dosage form according to the invention is preferably for oral administration, preferably in form of a tablet. According to this embodiment, a twice daily or thrice daily administration can be especially preferred since the preferred doses of the second pharmacologically active ingredient may be as high as 3,000/n mg, thus rendering a tablet containing e.g. a maximum of 3,000/2 mg or 3,000/3 mg, respectively, of the second pharmacologically active ingredient much more patient compliant.

In still another preferred embodiment, the pharmaceutical dosage form according to the invention is for administration once daily (n=1), wherein the pharmaceutical dosage form contains the first pharmacologically active ingredient in a dose of from 150/n to 1,200/n µg, preferably 200/n to 800/n µg, and the second pharmacologically active ingredient in a dose of from 100/n to 3,000/n mg. According to this embodiment, the pharmaceutical dosage form according to the invention is preferably for oral administration, preferably in form of a tablet.

In yet another preferred embodiment, the pharmaceutical dosage form according to the invention is for administration multiple daily (n=2, 3, 4, 5 or 6), wherein the pharmaceutical dosage form contains the first pharmacologically active ingredient in a dose of from 150/n to 1,200/n µg, preferably 200/n to 800/n µg, and the second pharmacologically active ingredient in a dose of from 100/n to 3,000/n mg. According to this embodiment, the pharmaceutical dosage form according to the invention is preferably for oral administration, preferably in form of a tablet. According to this embodiment, a twice daily or thrice daily administration can be especially preferred since the preferred doses of the second pharmacologically active ingredient may be as high as 3,000/n mg, thus rendering a tablet containing e.g. a maximum of 3,000/2 mg or 3,000/3 mg, respectively, of the second pharmacologically active ingredient much more patient compliant.

The pharmaceutical dosage form according to the invention may provide under in vitro conditions immediate release or controlled release of the first pharmacologically active ingredient and/or the second pharmacologically active ingredient. In vitro release is preferably determined in accordance with Ph. Eur., preferably paddle method with sinker, 75 rpm, 37° C., 900 mL artificial gastric juice, pH 6.8.

The first pharmacologically active ingredient and/or the second pharmacologically active ingredient may independently of one another be present in the pharmaceutical dosage form at least partially in controlled-release form. For example, the first pharmacologically active ingredient and/or the second pharmacologically active ingredient may be released from the pharmaceutical dosage form in a prolonged manner, e.g. if administered orally, rectally or percutaneously. Such pharmaceutical dosage forms are particularly useful for "once-daily" or "twice-daily" preparations, which only have to be taken once a day, respectively, twice a day. Suitable controlled-release materials are well known to those skilled in the art.

The pharmaceutical dosage form according to the invention providing controlled release of the first pharmacologically active ingredient and/or the second pharmacologically active ingredient may be produced using materials, means, devices and processes that are well known in the prior art of pharmaceutical dosage forms.

In order to obtain a solid pharmaceutical dosage form such as a tablet, for example, the pharmacologically active ingredients of the pharmaceutical composition may be granulated with a pharmaceutical carrier, for example conventional tablet ingredients such as corn starch, lactose, saccharose, sorbitol, talcum, magnesium stearate, dicalcium phosphate or pharmaceutically acceptable gums, and pharmaceutical diluents, for example water, in order to form a solid composition that contains the pharmacologically active ingredients in homogeneous distribution. The term "homogeneous distribution" is taken to mean that the pharmacologically active ingredients are distributed uniformly over the entire composition, so that said composition may easily be divided into equally effective dose units, such as tablets, pills or capsules and the like. The solid composition is then divided into dose units. The tablets or pills of the pharmaceutical composition according to the invention may also be coated or compounded in a different manner, in order to provide a dosage form with a controlled release.

If one of the pharmacologically active ingredients is to be released prior to the other pharmacologically active ingredient, for example at least 30 minutes or 1 hour beforehand, pharmaceutical dosage forms having a corresponding release profile may be prepared. An example of such a pharmaceutical dosage form is an osmotically-driven release system for achieving a delayed release of either the first or the second pharmacologically active ingredient from an inner part (core) of the pharmaceutical dosage form via a coating that itself contains the other pharmacologically active ingredient which is accordingly released earlier. In a release system of this kind, which is particularly suitable for oral administration, at least part, and preferably all, of the surface of the release system, preferably those parts that will come into contact with the release medium, is/are semipermeable, preferably equipped with a semipermeable coating, so the surface(s) is/are permeable to the release medium, but substantially, preferably entirely, impermeable to the pharmacologically active ingredient contained in the core, the surface(s) and/or optionally the coating comprising at least one opening for releasing the pharmacologically active ingredient contained in the core. Moreover, precisely that/those surface(s) that is/are in contact with the release medium is/are provided with a coating containing and releasing the other pharmacologically active ingredient. This is preferably taken to mean a system in tablet form comprising a release opening, a core containing the first or the second pharmacologically active ingredient, a polymer portion that exerts pressure upon swelling, a semipermeable membrane and a coating containing the other pharmacologically active ingredient. Embodiments and examples of osmotically-driven release systems are, for example, disclosed in U.S. Pat. Nos. 4,765,989, 4,783,337 and 4,612,008.

A further example of a suitable pharmaceutical dosage form is a gel-matrix tablet. Suitable examples are provided in U.S. Pat. Nos. 4,389,393, 5,330,761, 5,399,362, 5,472,711 and 5,455,046. Particularly suitable is a retarding matrix dosage form, with an inhomogeneous distribution of the pharmaceutical composition, whereby, for example, one pharmacologically active ingredient, i.e. the first or the second pharmacologically active ingredient, is distributed in the outer region (the portion that comes into contact with the release medium most quickly) of the matrix and the other pharmacologically active ingredient is distributed inside the matrix. On contact with the release medium, the outer matrix layer initially (and rapidly) swells and firstly releases the pharmacologically active ingredient contained therein, followed by the significantly (more) controlled release of the other pharmacologically active ingredient. Examples of a suitable matrix include matrices with 1 to 80% by weight of one or more hydrophilic or hydrophobic polymers as pharmaceutically acceptable matrix formers.

Preferably, the pharmaceutical dosage form according to the invention provides immediate release of the first pharmacologically active ingredient, and immediate or controlled release of the second pharmacologically active ingredient.

In a preferred embodiment, the pharmaceutical dosage form according to the invention provides immediate release of both, the first and the second pharmacologically active ingredient. In this particular case, a multiple daily administration, in particular an administration twice daily, thrice daily, or up to six times a day is preferred.

In another preferred embodiment, the pharmaceutical dosage form according to the invention provides immediate release of the first pharmacologically active ingredient, and controlled release of the second pharmacologically active ingredient. This release profile may be realized by employing the aforementioned methods, e.g. the osmotically-driven release system providing the first pharmacologically active ingredient in the coating and the second pharmacologically active ingredient in the core, or the retarding matrix dosage form containing the first pharmacologically active ingredient in the outer matrix layer and the second pharmacologically active ingredient in the inside of the matrix.

In yet another preferred embodiment, the pharmaceutical dosage form according to the invention provides controlled release of both the first and the second pharmacologically active ingredient.

In a further aspect, the invention relates to the use of the pharmaceutical composition according to the invention, and the pharmaceutical dosage form according to the invention respectively, in the prevention or treatment of pain.

In a preferred embodiment, the pharmaceutical composition according to the invention and the pharmaceutical dosage form according to the invention, respectively, are for use in the treatment of pain, wherein the pain is preferably
    peripheral, central or muscle skeletal pain; and/or
    acute, subacute or chronic pain; and/or
    moderate to severe pain; and/or neuropathic or psychogenic or nociceptive or mixed pain; and/or low back pain, visceral pain or headache; and/or post-operative (post-surgical), cancer or inflammatory pain.

For the purpose of specification, "acute pain" preferably refers to pain that lasts up to about 4 weeks, "subacute pain" preferably refers to pain that lasts from more than about 4 weeks to about 12 weeks, and "chronic pain" preferably refers to pain that lasts for more than about 12 weeks.

Preferably, the pain is selected from the group consisting of cancer pain, peripheral neuropathic pain, osteoarthritis, chronic visceral pain, neuropathic pain (diabetic polyneuropathy, HIV-associated neuropathic pain, posttraumatic neuropathic pain, postherpetic neuralgia, chemotherapy associated pain), postzosteric neuralgia, postoperative neuropathic pain, inflammatory pain, migraine, low-back pain, fibromyalgia and trigeminal neuralgia.

In a preferred embodiment, the pain is chronic pain, in particular chronic nociceptive pain and/or chronic inflammatory pain.

In another preferred embodiment, the pain is non-chronic or acute pain, in particular post-operative pain (post-surgical pain).

In a further preferred embodiment, the pain is selected from the group consisting of diabetic polyneuropathy, postzosteric neuralgia, postoperative neuropathic pain, low-back pain and fibromyalgia.

In the following, the doses of the first and the second pharmacologically active ingredient are again expressed according to the number of administrations "n" per day, i.e. the number of administrations of the pharmaceutical dosage form according to the invention in the course of 24 hours.

In a preferred embodiment, the pharmaceutical dosage form is for use in the treatment of neuropathic pain which may be optionally superimposed by nociceptive pain, where the dose of the first pharmacologically active ingredient contained in the pharmaceutical dosage form preferably is in the range of 1/n µg to 800/n µg or 1/n µg to 600/n µg or 1/n µg to 400/n µg or 1/n µg to 250/n µg, more preferably in the range of 5/n µg to 150/n µg, even more preferably in the range of 10/n µg to 100/n µg, most preferably in the range of 20/n µg to 80/n µg and in particular most preferably in the range of 30/n µg to 50/n µg. According to this embodiment, the dose of the second pharmacologically active ingredient contained in the pharmaceutical dosage form preferably is in the range of 100/n mg to 3,000/n mg.

In a preferred embodiment, in particular when the pharmaceutical dosage form is for use in the treatment of neuropathic pain and the second pharmacologically active ingredient is selected from acetylsalicyclic acid and the physiologically acceptable salts thereof, the dose of the first pharmacologically active ingredient contained in the pharmaceutical dosage form preferably is in the range of 1/n µg to 800/n µg or 1/n µg to 600/n µg or 1/n µg to 400/n µg or 1/n µg to 250/n µg, more preferably in the range of 5/n µg to 150/n µg, even more preferably in the range of 10/n µg to 100/n µg, most preferably in the range of 20/n µg to 80/n µg and in particular most preferably in the range of 30/n µg to 50/n µg; and the dose of the second pharmacologically active ingredient contained in the pharmaceutical dosage form preferably is in the range of 100/n mg to 5,000/n mg, more preferably in the range of 250/n mg to 4,500/n mg, even more preferably in the range of 500/n mg to 4,000/n mg, most preferably in the range of 750/n mg to 3,500/n mg and in particular in the range of 1,000/n mg to 3,000/n mg.

In another preferred embodiment, the pharmaceutical dosage form is for use in the treatment of nociceptive pain which may be optionally superimposed by neuropathic pain, where the dose of the first pharmacologically active ingredient contained in the pharmaceutical dosage form preferably is in the range of 50/n µg to 2,000/n µg or 50/n µg to 1,400/n µg or 50/n µg to 1,200/n µg or 50/n µg to 1,000/n µg, more preferably in the range of 100/n µg to 800/n µg, still more preferably in the range of 150/n µg to 650/n µg, even more preferably in the range of 250/n µg to 550/n µg, and most preferably in the range of 350/n µg to 450/n µg. According to this embodiment, the dose of the second pharmacologically active ingredient contained in the pharmaceutical dosage form preferably is in the range of 100/n mg to 3,000/n mg.

In a preferred embodiment, in particular when the pharmaceutical dosage form is for use in the treatment of nociceptive pain and the second pharmacologically active ingredient is selected from acetylsalicyclic acid and the physiologically acceptable salts thereof, the dose of the first pharmacologically active ingredient contained in the pharmaceutical dosage form preferably is in the range of 50/n µg to 2,000/n µg or 50/n µg to 1,400/n µg or 50/n µg to 1,200/n µg or 50/n µg to 1,000/n µg, more preferably in the range of 100/n µg to 800/n µg, still more preferably in the range of 150/n µg to 650/n µg, even more preferably in the range of 250/n µg to 550/n µg, and most preferably in the range of 350/n µg to 450/n µg; and the dose of the second pharmacologically active ingredient contained in the pharmaceutical dosage form preferably is in the range of 100/n mg to 5,000/n mg, more preferably in the range of 250/n mg to 4,500/n mg, even more preferably in the range of 500/n mg to 4,000/n mg, most preferably in the range of 750/n mg to 3,500/n mg and in particular in the range of 1,000/n mg to 3,000/n mg.

Preferably, the pharmaceutical composition contains the first and the second pharmacologically active ingredient in such a weight ratio that they will exert a synergistic therapeutic effect upon administration to a patient. Thereby, the term "synergistic therapeutic effect" may refer to a synergistic therapeutic effect with respect to the prevention or treatment of pain (synergistic analgesic effect), a synergistic therapeutic effect with respect to the prevention or treatment of anxiety (synergistic anxiolytic effect) as well as a synergistic therapeutic effect with respect to the prevention or treatment of epilepsy (synergistic anti-convulsive effect). Suitable weight ratios of the pharmacologically active ingredients generating the synergistic therapeutic effect can be determined by methods well known to those skilled in the art.

A further aspect of the invention relates to a method of treating or preventing pain comprising the preferably twice daily or once daily, preferably oral administration of the pharmaceutical dosage form according to the invention to a subject in need thereof.

In a particular preferred embodiment, the first pharmacologically active ingredient is (1r,4r)-6'-fluoro-N,N-dimethyl-4-phenyl-4',9'-dihydro-3'H-spiro[cyclohexane-1,1'-pyrano[3,4,b]indol]-4-amine according to formula (I) in form of its free base, or a hemicitrate, hydrochloride or maleate salt thereof; and/or the second pharmacologically active ingredient is selected from acetylsalicylic acid and the physiologically acceptable salts thereof; and/or the pharmaceutical composition and the pharmaceutical dosage form, respectively, contain the first pharmacologically active ingredient in a dose of from 20 µg to 80 µg or of from 80 µg to 200 µg or of from 200 µg to 800 µg or of from 800 µg to 1,200 µg; and/or the pharmaceutical composition and the pharmaceutical dosage form, respectively, contain the second pharmacologically active ingredient in a dose of from 50 to 5,000 mg; in particular 50 mg to 4,000 mg, and/or the relative weight ratio of the first pharmacologically active ingredient to the second pharmacologically active ingredient is within the range of from 1:30 to 1:1,000,000, preferably 1:500 to 1:500,000. in the pharmaceutical composition and the pharmaceutical dosage form, respectively; and/or the pharmaceutical composition is for use in the treatment of pain; wherein the pain is peripheral, central or muscle skeletal pain; and/or acute, subacute or chronic pain; and/or moderate to severe pain; and/or neuropathic or psychogenic or nociceptive or mixed pain; and/or low back pain, visceral pain or headache; and/or post-operative (post-surgical), cancer or inflammatory pain; and/or the pharmaceutical composition and the pharmaceutical dosage form, respectively, contain the first pharmacologically active ingredient and the second pharmacologically active ingredient in such a weight ratio that upon administration to a patient they will exert a synergistic therapeutic effect; and/or the pharmaceutical dosage form provides immediate release of the first pharmacologically active ingredient in vitro in accordance with Ph. Eur.; and/or the pharmaceutical dosage form provides immediate or controlled release of the second pharmacologically active ingredient in vitro in accordance with Ph. Eur.; and/or the pharmaceutical dosage form is for oral administration; and/or the pharmaceutical dosage form is for administration once, twice or thrice daily.

In a further aspect, the invention relates to a kit comprising a first pharmaceutical dosage form comprising the first pharmacologically active ingredient as described above, and a second pharmaceutical dosage form comprising the second pharmacologically active ingredient as described above.

A suitable embodiment is a kit in which the first pharmaceutical dosage from comprising the first pharmacologically active ingredient and the second pharmaceutical dosage form comprising the second pharmacologically active ingredient, although spatially separated, are provided in a common presentation form, e.g. packaging.

Preferably, the first and the second pharmaceutical dosage form are adapted for simultaneous or sequential administration, wherein the first pharmaceutical dosage form may be administered before or after the second pharmaceutical dosage form and wherein the first and the second pharmaceutical dosage form are administered either via the same or a different pathway of administration.

For the purpose of specification, the term "simultaneous administration" preferably refers to an administration of the first and the second pharmaceutical dosage form within a time span of 15 minutes from each other, whereas the term "sequential administration" preferably refers to an administration of the first and the second pharmaceutical dosage form within a time span of more than 15 minutes from each other.

In a preferred embodiment, the first and the second pharmaceutical dosage form are adapted for administration to the patient via the same pathway.

In another preferred embodiment, the first and the second pharmaceutical dosage form are adapted for administration to the patient via different pathways.

In a preferred embodiment, the first and the second pharmaceutical dosage form are administered simultaneously.

In another preferred embodiment, the first and the second pharmaceutical dosage form are administered sequentially.

In a preferred embodiment, the first and/or the second pharmaceutical dosage form are adapted for once daily administration.

In another preferred embodiment, the first and/or the second pharmaceutical dosage form are adapted for multiple daily administration, in particular twice daily or thrice daily.

In a preferred embodiment, the first pharmaceutical dosage form is adapted for once daily administration and the second pharmaceutical dosage form is adapted for multiple daily, in particular twice daily or thrice daily, administration.

Suitable pathways of administration of the pharmaceutical dosage forms contained in the kit include but are not limited to oral, intravenous, intraperitoneal, intradermal, intrathecal, intramuscular, intranasal, transmucosal, subcutaneous, and/or rectal administration.

In a preferred embodiment, one or both of the pharmaceutical dosage forms contained in the kit are for oral administration.

In another preferred embodiment, one or both of the pharmaceutical dosage forms contained in the kit are for parenteral administration, in particular intravenous, intraperitoneal, intrathecal, intramuscular, or subcutaneous administration.

In a preferred embodiment, the first and the second pharmaceutical dosage form are for oral, simultaneous administration once daily.

In another preferred embodiment, the first and the second pharmaceutical dosage form are for oral, simultaneous administration multiple daily, in particular twice daily or thrice daily.

In still another preferred embodiment, the first and the second pharmaceutical dosage form are each for oral, sequential administration once daily.

In a preferred embodiment, the first and the second pharmaceutical dosage form are for sequential administration once daily each, where the first and the second pharmaceutical dosage form are adapted for administration via different pathways, e.g. oral and parenteral administration.

In another preferred embodiment, the first and the second pharmaceutical dosage form are each for oral, sequential administration multiple daily, in particular twice daily or thrice daily.

In another preferred embodiment, the first and the second pharmaceutical dosage form are for sequential administration multiple daily each, in particular twice daily or thrice daily, where the first and the second pharmaceutical dosage form are adapted for administration via different pathways, e.g. oral and parenteral administration.

The following examples further illustrate the invention but are not to be construed as limiting its scope.

Pharmacological Methods:

In the following, the first pharmacologically active ingredient (1r,4r)-6'-fluoro-N,N-dimethyl-4-phenyl-4',9'-dihydro-3'H-spiro[cyclohexane-1,1'-pyrano[3,4,1D]indol]-4-amine was employed in form of the hemicitrate salt. Therefore, all amounts of the first pharmacologically active ingredient are specified with respect to the hemicitrate salt.

As the second pharmacologically active ingredient, acetylsalicylic acid was employed.

Paw Incision Model in Rats (Postoperative Pain)

The experiments were carried out in male albino rats (Sprague Dawley) with 170 g-230 g body weight from a commercial breeder (Janvier; France). The animals were housed under standardized conditions: light/dark rhythm (06.00 h-18.00 h light, 18.00 h-06.00 h dark); room temperature 20° C.-24° C.; relative air humidity 35%-70%; 15 air changes per hour, air movement<0.2 m/sec. The animals were given tap water and a diet of standard laboratory food (Ssniff R/M-Haltung, Ssniff Spezialdiäten GmbH, Soest, Germany) ad libitum. Both were withdrawn during the test. All rats were used only once. Ten rats were used per experimental group. There were at least five days between delivery of the animals and the day of surgery.

The rats were placed in a plastic cage with a wire mesh bottom which allowed full access to the paws. Hind paw withdrawal threshold after mechanical stimulation was tested with electronic von Frey hairs (Somedic Sales AB, Horby, Sweden). Animals were placed in a plastic cage with a wire mesh bottom which allowed full access to the paws. Behavioral accommodation was allowed for 30 min. In each case, withdrawal response was measured at an area adjacent to the wound (ipsilateral) and to the same area on the non-injured foot (contralateral). Two hours after surgery, primary hypersensitivity was tested as tactile withdrawal threshold shortly before drug administration and at different time points after drug application. Animals injected with vehicle served as controls. The pretest measurement was made prior to surgery and two thresholds were taken per test and averaged.

Surgery was performed as previously described (Brennan T. J., Vandermeulen E. P., and Gebhart G. F., Characterization of a rat model of incisional pain, Pain 1996; 64:493-501). Briefly, rats were anaesthetised with isoflurane, and a 1 cm longitudinal incision was made, through skin and fascia of the plantar aspect of the foot, starting from the proximal edge of the heel and extending toward the metatarsal toes. The plantaris muscle was elevated and incised longitudinally. The muscle origin and insertion remained intact. After spreading of the muscle and haemostasis with gentle pressure, the skin was closed with two single interrupted sutures. After surgery, the rats were allowed to recover in their home cages and the animals regained consciousness within 2 to 5 minutes. In order to ensure a complete recovery from anaesthesia the baseline value of each individual animal was recorded not until 2 hours after surgery.

The first pharmacologically active ingredient was dissolved in 5% DMSO and 95% glucose solution (5%). The second pharmacologically active ingredient was dissolved in 1% CMC in aqua dest. Intravenous (i.v.) and intraperitoneal (i.p.) applications were made in a volume of 5 mL/kg.

Data were recorded and the median was calculated from five values of each animal and measurement.

The median values of the individual latencies are calculated as the percentage of the Maximum Possible Effect (% MPE) according to the following formula:

% MPE=100−[(value after application−pretest before surgery)/(pretest after surgery−pretest before surgery)·100]

The individual % MPE values were averaged for the respective treatment group and expressed as mean % MPE±standard error of the mean (SEM).

The pharmacologically active ingredients were administered using a logarithmically staggered dose scheme. The results are presented in graphs as means±SEM against the time after surgery.

Data were analyzed by means of two-factor analysis of variance (ANOVA) with repeated measures. Significance of treatment-, time- or treatment×time interaction effects was analyzed by means of Wilks' Lambda statistics. In case of a significant treatment effect, pair-wise comparison was performed at the different time points effect by Fisher's least significant difference test. Results were considered statistically significant if $p<0.05$.

The interaction studies presented herein were performed by comparison of the theoretically additive effect of defined doses of the first and the second pharmacologically active ingredient with the experimental determined effect of their combination.

The application route was intravenous (i.v.) for the first pharmacologically active ingredient and intraperitoneal (i.p.) for the second pharmacologically active ingredient.

Tests were performed using doses of 0.00215 mg/kg body weight to 0.00681 mg/kg body weight of the first pharmacologically active ingredient and 100 mg/kg body weight of acetylsalicylic acid as the second pharmacologically active ingredient.

The time point of efficacy-calculation in case of the combined administration of the first and the second pharmacologically active ingredient according to the invention corresponds to the timepoint of the peak effect of the respective pharmacologically active ingredient. The effect of the experiments with fixed dose combinations showed higher experimental determined efficacy than the theoretically calculated efficacy. Thus, the combination studies demonstrate significant synergistic interaction of the first pharmacologically active ingredient with the second pharmacologically active ingredient.

When administered in combination, the first pharmacologically active ingredient (0.00464 mg/kg body weight i.v.) and the second pharmacologically active ingredient (acetylsalicylic acid, 100 mg/kg body weight i.p.) showed an analgesic efficacy with a maximal effect of 49% MPE at 30 min.

The analysis showed synergistic interaction of the first pharmacologically active ingredient and the second pharmacologically active ingredient 30 min. after administration.

Figure 1:
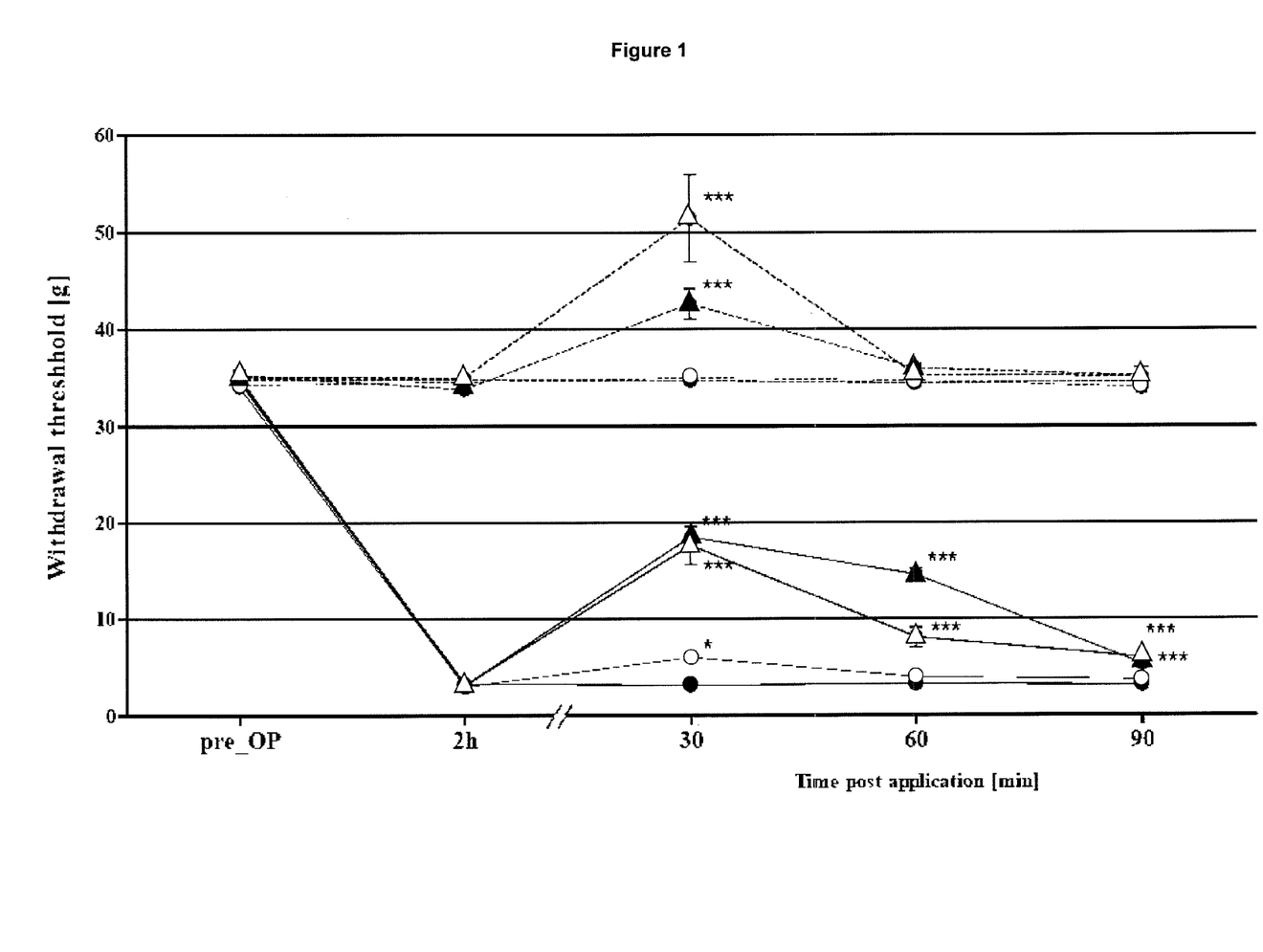
FIG. 1 shows the withdrawal threshold in g in dependence of the time elapsed after administration.

FIG. 1 shows the withdrawal threshold in g in dependence of the time elapsed after administration.

| | dose [mg/kg] | |
|---|---|---|
| ● | 0.0 + 0.0 | vehicle |
| ○ | 0.00215 + 100 | first pharmacologically |
| ▲ | 0.00464 + 100 | active ingredient + second |
| △ | 0.00681 + 100 | pharmacologically active ingredient |

— ipsilateral
----- contralateral
OP: operation

Figure 2:
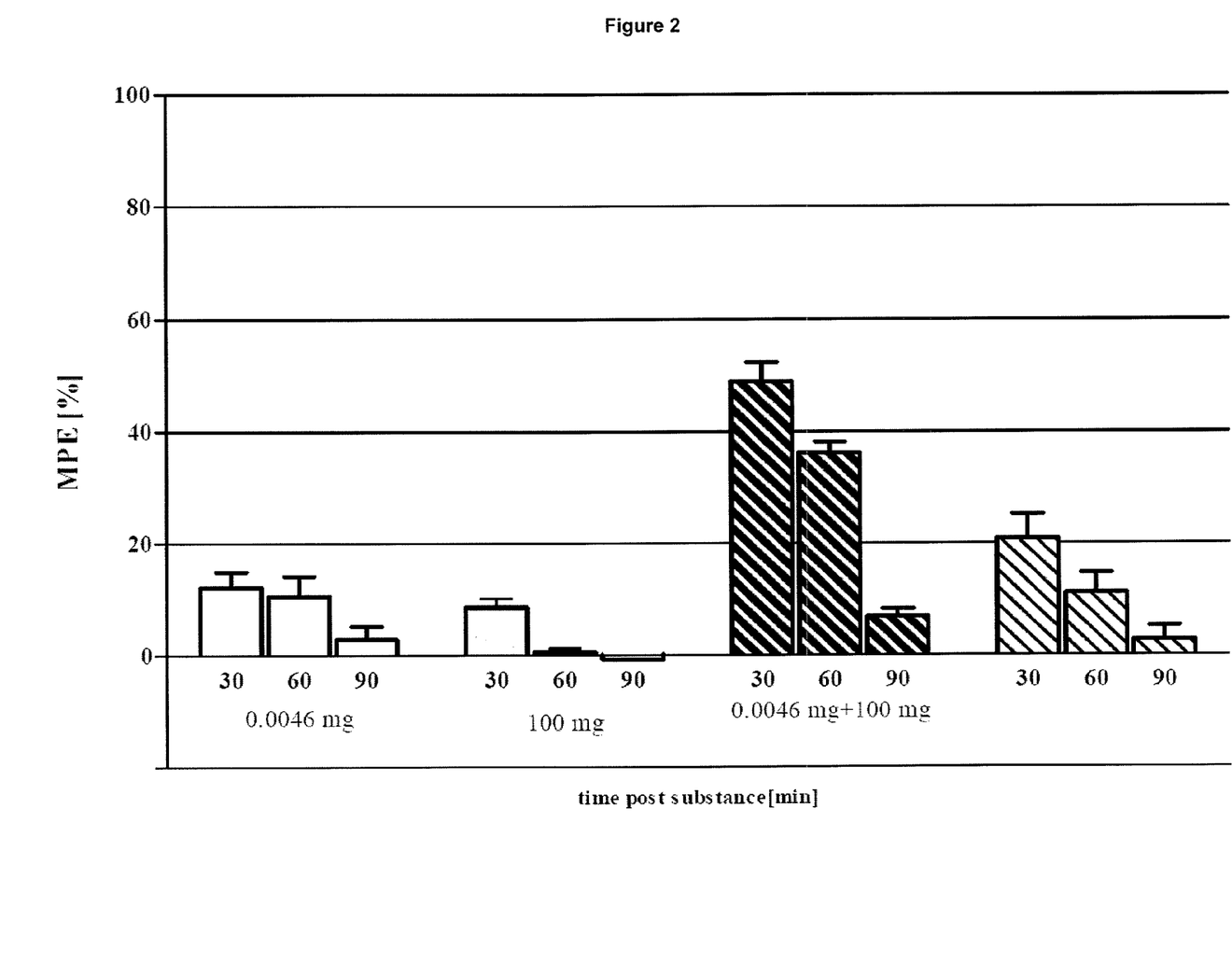
FIG. 2 shows % MPE (Maximum possible effect) of the first and the second pharmacologically active ingredient and of the combined administration of the first and the second pharmacologically active ingredient, and the theoretical % MPE of the combined administration of the first and the second pharmacologically active ingredient in dependence of the time post administration.

FIG. 2 shows % MPE (Maximum possible effect) of the first and the second pharmacologically active ingredient and of the combined administration of the first and the second pharmacologically active ingredient, and the theoretical % MPE of the combined administration of the first and the second pharmacologically active ingredient in dependence of the time post administration.

| | | dose [mg/kg] |
|---|---|---|
| ▭ | first pharmacologically active ingredient | 0.00464 |
| ▬ | second pharmacologically active ingredient | 100 |
| ▨ | combined administration of first pharmacologically active ingredient + second pharmacologically active ingredient | 0.00464 + 100 |
| ▨ | theoretical additive value of first pharmacologically active ingredient + second pharmacologically active ingredient | |

Experimental results demonstrating supra-additive effect of the combination of the first and the second pharmacologically active ingredient are summarized in the following tables 1 to 5.

TABLE 1

% MPE (Maximum possible effect) of the combined administration of different doses of the first and the second pharmacologically active ingredient in dependence of the time post administration:

| | | % MPE | | |
|---|---|---|---|---|
| | dose [mg/kg] | 30 min. (n = 10) Mean SEM | 60 min. (n = 10) Mean SEM | 90 min. (n = 10) Mean SEM |
| vehicle | 0.0 + 0.0 | −0.49 ± 0.69 | 0.00 ± 0.72 | −0.47 ± 0.99 |
| Combination of first pharmacologically active ingredient and second pharmacologically active ingredient | 0.00215 + 100 | 9.75 ± 1.29 p ≤ 0.001 | 3.17 ± 0.84 n.s. | 2.23 ± 0.85 n.s. |
| | 0.00464 + 100 | 48.9 ± 3.47 p ≤ 0.001 | 36.2 ± 2.02 p ≤ 0.001 | 6.92 ± 1.41 p ≤ 0.001 |
| | 0.00681 + 100 | 45.4 ± 5.54 p ≤ 0.001 | 15.4 ± 2.69 p ≤ 0.001 | 8.81 ± 1.16 p ≤ 0.001 | p: level of statistical significance; n.s.: not significant

TABLE 2

% MPE: GLM Repeated Measures and Statistical evaluation of the data following two-factor analysis of variance (ANOVA) and Fisher's LSD:

| GLM (General Linear Model) % MPE | | |
|---|---|---|
| treatment | time | interaction |
| $F(3, 31) = 124.51$ | $F(2, 62) = 168.462$ | $F(6, 62) = 51.616$ |
| $p < 0.001$ | $p < 0.001$ | $p < 0.001$ |

| ANOVA [Fisher's LSD] | | | |
|---|---|---|---|
| dose [mg/kg] | 30 min. | 60 min. | 90 min. |
| 0.00215 + 100 | $p = 0.001$ | $p = 0.125$ | $p = 0.086$ |
| 0.00464 + 100 | $p < 0.001$ | $p < 0.001$ | $p < 0.001$ |
| 0.00681 + 100 | $p < 0.001$ | $p < 0.001$ | $p < 0.001$ | p: level of statistical significance.

TABLE 3 ipsilateral: GLM Repeated Measures and Statistical evaluation of the data following two-factor analysis of variance (ANOVA) and Fisher's LSD:

| GLM (General Linear Model) ipsilateral | | |
|---|---|---|
| treatment | time | interaction |
| $F(3, 31) = 111.0$ $p < 0.001$ | $F(2, 62) = 174.9$ $p < 0.001$ | $F(6, 62) = 54.0$ $p < 0.001$ |

| ANOVA [Fisher's LSD] | | | |
|---|---|---|---|
| dose [mg/kg] | 30 min. | 60 min. | 90 min. |
| 0.00215 + 100 | $p = 0.016$ | $p = 0.325$ | $p = 0.253$ |
| 0.00464 + 100 | $p < 0.001$ | $p < 0.001$ | $p < 0.001$ |
| 0.0068 + 100 | $p < 0.001$ | $p < 0.001$ | $p < 0.001$ | p: level of statistical significance.

TABLE 4 contralateral: GLM Repeated Measures and Statistical evaluation of the data following two-factor analysis of variance (ANOVA) and Fisher's LSD:

| GLM (General Linear Model) contralateral | | |
|---|---|---|
| treatment | time | interaction |
| $F(3, 31) = 16.287$ | $F(2, 62) = 52.041$ | $F(6, 62) = 16.201$ |
| $p < 0.001$ | $p < 0.001$ | $p < 0.002$ |

| ANOVA [Fisher's LSD] | | | |
|---|---|---|---|
| dose [mg/kg] | 30 min. | 60 min. | 90 min. |
| 0.00215 + 100 | $p = 0.884$ | $p = 0.699$ | $p = 0.414$ |
| 0.00464 + 100 | $p < 0.001$ | $p = 0.272$ | $p = 0.436$ |
| 0.0068 + 100 | $p < 0.001$ | $p = 0.297$ | $p = 0.541$ | p: level of statistical significance.

TABLE 5

% MPE (Maximum possible effect) of the first and the second pharmacologically active ingredient and of the combined administration of the first and the second pharmacologically active ingredient, and the theoretical % MPE of the combined administration of the first and the second pharmacologically active ingredient in dependence of the time post administration and analysis of the interaction between the first and the second pharmacologically active ingredient:

| | dose [mg/kg] | % MPE 30 min. (n = 10) Mean SEM | 60 min. (n = 10) Mean SEM | 90 min. (n = 10) Mean SEM |
|---|---|---|---|---|
| first pharmacologically active ingredient | 0.00464 | 12.2 ± 2.69 | 10.6 ± 3.51 | 2.88 ± 2.27 |
| second pharmacologically active ingredient | 100 | 8.59 ± 1.67 | 0.52 ± 0.68 | 0.2 ± 1.36 |
| combination of first pharmacologically active ingredient and second pharmacologically active ingredient | 0.00464/100 | 48.9 ± 3.47 (theoretical additive value: 20.8 ± 4.48) $p < 0.001$ | 36.2 ± 2.02 (theoretical additive value: 11.1 ± 3.57) $p < 0.001$ | 6.9 ± 1.41 (theoretical additive value: 2.81 ± 2.41) $p = 0.015$ |

The invention claimed is:

1. A pharmaceutical dosage form comprising a pharmaceutical composition, wherein the pharmaceutical composition comprises:
   (a) a first pharmacologically active ingredient selected from the compound according to formula (I)

(I)

and the physiologically acceptable salts thereof, and
   (b) a second pharmacologically active ingredient which is a salicylic acid component selected from the group consisting of acetylsalicylic acid, salicylic acid, salicylamide, ethenzamide, salsalate, dipyrocetyl, benorilate, diflunisal, guacetisal, and the physiologically acceptable salts thereof;

wherein the pharmaceutical dosage form contains the first pharmacologically active ingredient in a dose of from 10 to 1,200 μg; and wherein the pharmaceutical dosage form contains the second pharmacologically active ingredient in a dose of from 50 to 5,000 mg.

2. The pharmaceutical dosage form according to claim 1, wherein the first pharmacologically active ingredient is the compound according to formula (I)

(I)

3. The pharmaceutical dosage form according to claim 1, wherein the second pharmacologically active ingredient is selected from acetylsalicylic acid and the physiologically acceptable salts thereof.

4. The pharmaceutical dosage form according to claim 1, wherein the relative weight ratio of the first pharmacologically active ingredient to the second pharmacologically active ingredient is within the range of from 1:42 to 1:500,000.

5. A method for preventing or treating pain, comprising administering to a patient a therapeutically effective amount of the pharmaceutical dosage form according to claim 1.

6. The method according to claim 5, wherein the pain is:
peripheral, central or muscle skeletal pain; and/or
acute, subacute or chronic pain; and/or
moderate to severe pain; and/or
neuropathic or psychogenic or nociceptive or mixed pain; and/or
low back pain, visceral pain or headache; and/or
post-operative, post-surgical, cancer or inflammatory pain.

7. The pharmaceutical dosage form according to claim 1, which is for oral, intravenous, intraperitoneal, transdermal, intrathecal, intramuscular, intranasal, transmucosal, subcutaneous, or rectal administration.

8. The pharmaceutical dosage form according to claim 1, which provides under in vitro conditions immediate release or controlled release of the first pharmacologically active ingredient and/or the second pharmacologically active ingredient.

9. A kit comprising a first pharmaceutical dosage form comprising the first pharmacologically active ingredient as defined in claim 1 and a second pharmaceutical dosage form comprising the second pharmacologically active ingredient as defined in claim 1.

10. The kit according to claim 9, wherein the first and the second pharmaceutical dosage form are adapted for simultaneous or sequential administration, either by the same or a different pathway of administration.

* * * * *